United States Patent [19]

Morimoto et al.

[11] Patent Number: 5,648,531
[45] Date of Patent: Jul. 15, 1997

[54] PROCESS FOR PRODUCING ACETIC ANHYDRIDE ALONE OR ACETIC ANHYDRIDE AND ACETIC ACID

[75] Inventors: Yoshiaki Morimoto; Hiroto Tanigawa; Kazuyuki Akita, all of Hyogo, Japan

[73] Assignee: Daicel Chemical Industries, Ltd., Osaka, Japan

[21] Appl. No.: 406,896

[22] PCT Filed: Aug. 16, 1994

[86] PCT No.: PCT/JP94/01354

§ 371 Date: Mar. 22, 1995

§ 102(e) Date: Mar. 22, 1995

[87] PCT Pub. No.: WO95/05356

PCT Pub. Date: Feb. 23, 1995

[30] Foreign Application Priority Data

Aug. 18, 1993 [JP] Japan ................ 5-203896

[51] Int. Cl.⁶ .................. C07C 51/56; C07C 51/54
[52] U.S. Cl. .................. 562/891; 562/519; 562/890; 562/517
[58] Field of Search .................. 562/519, 608, 562/517, 891, 890

[56] References Cited

U.S. PATENT DOCUMENTS

| 4,102,922 | 7/1978 | Price | 206/532 |
|---|---|---|---|
| 4,364,907 | 12/1982 | Barnes | 423/22 |
| 4,374,070 | 2/1983 | Larkins et al. | 260/549 |
| 4,476,238 | 10/1984 | Palmer et al. | 502/31 |
| 5,362,365 | 11/1994 | Niijima et al. | 203/31 |
| 5,380,929 | 1/1995 | Erpenbach et al. | 562/519 |

FOREIGN PATENT DOCUMENTS

| 0081732 | 6/1983 | European Pat. Off. . | |
| 0497521 | 5/1992 | European Pat. Off. | C07C 53/08 |
| 0535825 | 4/1993 | European Pat. Off. . | |

*Primary Examiner*—C. Warren Ivy
*Assistant Examiner*—Rosalynd Williams
*Attorney, Agent, or Firm*—Flynn, Thiel, Boutell & Tanis, P.C.

[57] ABSTRACT

A process for continuously producing acetic anhydride alone or acetic anhydride and acetic acid by reacting methyl acetate and/or dimethyl ether and, optionally, water and/or methanol, with carbon monoxide alone or carbon monoxide and hydrogen in the presence of a rhodium compound and methyl iodide as principal catalysts. Trace impurities causative of tar formation are distilled and separated in an evaporator and/or a subsequent refining step to remove the same. The removal of the trace impurities causative of tar formation serves to decrease the amount of tar formed as an impurity.

14 Claims, 1 Drawing Sheet

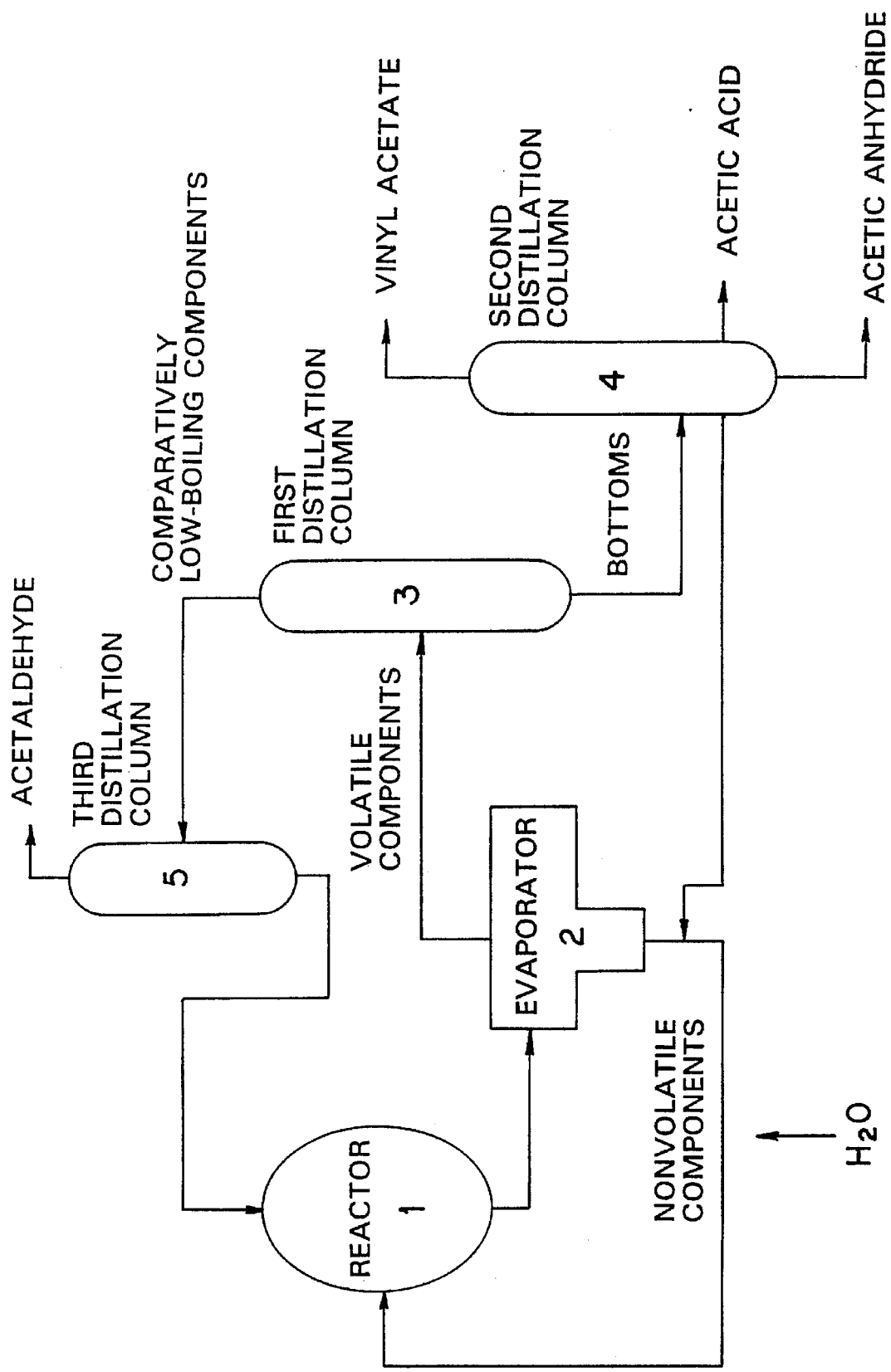

PROCESS FOR PRODUCING ACETIC ANHYDRIDE ALONE OR ACETIC ANHYDRIDE AND ACETIC ACID

The present invention relates to a process for producing acetic anhydride alone or acetic anhydride and acetic acid by reacting methyl acetate and/or dimethyl ether and optionally water and/or methanol with carbon monoxide alone or carbon monoxide and hydrogen in the presence of a rhodium compound and methyl iodide as the principal catalysts.

RELATED ART

Acetic acid is an essential compound necessary in many industries, including the polymer industry and the chemical industry, wherein acetic acid is used in a large amount as a starting material of acetic esters, acetic anhydride, vinyl acetate, and terephthalic acid. On the other hand, acetic anhydride not only is used in a large amount as a starting material of cellulose acetate, but also is a useful compound as a starting material of chemicals such as drugs, perfumes, and dyes. Further, acetic acid and acetic anhydride are mutually related compounds in practical uses. For example, in the cellulose acetate industry, acetic anhydride is produced from acetic acid and then reacted with cellulose to give cellulose acetate and acetic acid, which is reused.

Although acetic anhydride has heretofore been produced from ketene obtained by thermal decomposition of acetic acid, there has recently been developed a process wherein acetic anhydride is produced from methyl acetate or dimethyl ether, and carbon monoxide. A reaction involved in this process is a catalytic reaction wherein a rhodium compound and methyl iodide are used as the principal catalysts. Since the reaction rate is low when only the principal catalysts are used, however, various promoters have been proposed.

A function required of the promotors is to promote the reaction of methyl acetate or dimethyl ether with carbon monoxide to such an extent as to enable the reaction to be industrially operable. A desirable promoter is one which can exhibit a great reaction-promoting effect even when added in an amount as small as possible and helps reduce the formation of by-products, including tar.

Although various promoters have been proposed for this purpose, the formation of such by-products is not always dependent on the kind of promoter alone. A primary factor in the formation of these by-products is believed to be a rhodium hydride complex formed by a reaction of the rhodium compound as one of the principal catalysts with hydrogen present in the liquid reaction mixture. Since rhodium serves as a catalyst in the main reaction, the concentration thereof in the liquid reaction mixture must be maintained at a necessary level. On the other hand, hydrogen is necessary for enabling rhodium as one of the principal catalysts to be maintained in a highly active monovalent state, and must therefore be fed together with carbon monoxide as starting materials into a reactor according to known techniques (U.S. Pat. No. 4,374,070).

Further, as the partial pressure of hydrogen in the gaseous phase portion in the reactor is increased, the amount of the by-products formed is increased. Aside from the magnitude of the amount of the by-products formed, this tendency is always recognized, even when any promoter is used. Accordingly, it is a known fact that it is important in industrially carrying out the reaction to maintain the partial pressure of hydrogen in the gaseous phase portion in the reactor at a necessary but minimum and constant level.

In view of the foregoing, U.S. Pat. No. 4,384,907 discloses a method of removing tar formed as a by-product, wherein tar extracted with an aqueous solution of HI is further extracted with aqueous ammonia to recover an additional amount of rhodium from the tar. However, this method necessarily involves the use of ammonia and subsequent removal of the ammonia from the process stream that must be returned to the reaction. Although various other methods have been attempted (U.S. Pat. No. 4,476,238), the fact is that no methods of easily and effectively removing tar have been found yet. Further, the presence of tar sometimes decreases the catalytic activity of the catalysts, and entrap the catalysts of an iodine and a noble metal to inactivate the catalyst and terminate the carbonylation reaction. It is therefore desired that as little tar, if any, as possible exists in the reaction system.

BRIEF DESCRIPTION OF THE DRAWING

FIG. 1 is a flow diagram of an example of the process for producing acetic acid and acetic anhydride according to the present invention.

In FIG. 1, reference numeral 1 refers to a reactor, 2 to an evaporator, 3 to the first distillation column, 4 to the second distillation column, and 5 to the third distillation column.

DISCLOSURE OF THE INVENTION

The inventors of the present invention have found out that there is a close correlation between the amount of tar formed and the concentrations of by-products such as acetaldehyde, vinyl acetate and ethylidene diacetate formed in trace amounts simultaneously with the production of acetic anhydride alone or acetic acid and acetic anhydride with production equipment including a series of continuous units. More specifically, they have completed an effective process capable of remarkably decreasing the amount of tar formed as a by-product in a reactor or the subsequent evaporator by preventing the accumulation of at least one component of these by-products.

Specifically, the present invention relates to a process for continuously producing acetic anhydride alone or acetic anhydride and acetic acid by continuously reacting dimethyl ether and/or methyl acetate and, optionally, water and/or methanol with carbon monoxide or carbon monoxide and hydrogen in the presence of a rhodium compound and methyl iodide as the principal catalysts, wherein trace impurities causative of tar formation are separated in an evaporator and/or the subsequent refining step to remove the same.

The present invention provides a process for producing acetic anhydride alone or acetic anhydride and acetic acid by continuously reacting dimethyl ether and/or methyl acetate and, optionally, water and/or methanol, with carbon monoxide alone or carbon monoxide and hydrogen in the presence of a rhodium compound and methyl iodide as the principal catalysts in a carbonylation reactor, introducing the resulting liquid reaction mixture into an evaporator having a pressure lower than that of the reactor to separate the reaction mixture into a volatile phase containing the product, unreacted dimethyl ether and/or methyl acetate, and methyl iodide, and a nonvolatile phase containing the rhodium compound, distilling the volatile phase to obtain the product and a distillate containing the unreacted dimethyl ether and/or methyl acetate and methyl iodide, and recirculating the liquid distillate to the reactor while recirculating the nonvolatile phase containing and rhodium compound to the reactor, wherein trace impurities causative of tar formation are distilled in an evaporator of the distillation column type and/or distilled and separated in the subsequent refining step.

According to the present invention, the acetaldehyde and/or vinyl acetate formed as by-product(s) in the reactor or the following evaporator is separated and removed in the evaporator and/or the subsequent refining step to minimize the amount of tar formed as a by-product. Further, the ethylidene diacetate formed as a by-product in the reactor or in the following evaporator is decomposed by adding water to the catalyst solution to be recycled from the evaporator vessel to the reactor.

Compounds that can be suitably used as the starting materials in the present invention are methyl acetate, dimethyl ether, and methanol. The amount off methanol that may be used as the starting material for the reaction is closely correlated with the amount of the acetic acid to be produced. Accordingly, use of methanol may be dispensed with if necessary. Methyl acetate and dimethyl ether may be used simultaneously. Further, water may be used if necessary. Carbon monoxide is used as another starting material to be fed into the reactor, and a small amount of hydrogen gas may additionally be fed into the reactor as is already known (U.S. Pat. No. 4,374,070). The amount of hydrogen gas that may be fed into the reactor may be such that the partial pressure of hydrogen inside the reactor is at least 0.5 atm. The partial pressure of hydrogen is preferably at most 5 atm. The partial pressure of carbon monoxide may be in the range of 10 to 100 atm.

Any kind of rhodium compound may be used as one of the principal catalysts for the reaction in so far as it can be dissolved in the liquid reaction mixture under reaction conditions. Usable examples of the rhodium compound include inorganic salts of rhodium, such as halide, nitrate, and sulfate of rhodium; organic acid salts of rhodium, such as carboxylates of rhodium; and organorhodium complexes having carbon monoxide, an amine or a phosphine coordinated with rhodium. The concentration of rhodium is preferably 100 to 3,000 ppm. The concentration of methyl iodide as another principal catalyst for the first carbonylation reaction in the liquid reaction mixture may be in the range of 5 to 30 wt.

The reaction is carried out under a reaction pressure of 10 to 100 atm, preferably 20 to 50 atm, at a temperature of 150 to 250° C.

Acetic anhydride and/or acetic acid is preferably used as a reaction solvent, though other organic solvents slay be used as well. The mode of the reaction may be either a batch-wise reaction mode or a continuous reaction mode. From a more practical point of view, however, a continuous reaction mode is preferred.

A description will now be made of an example of the process according to the present invention while referring to FIG. 1. When the reaction is carried out according to the continuous reaction mode, the starting materials, the catalysts and the solvent are continuously fed into a reactor (1). The liquid reaction mixture in the reactor is continuously withdrawn therefrom and introduced into an evaporator (2) having a pressure lower than that of the reactor to separate the product therefrom. In this step, the product may be withdrawn either in the form of vapor or in the form of the reaction liquid.

Acetic anhydride as the product, methyl iodide as one of the catalysts, unreacted methyl acetate and/or dimethyl ether, acetic acid as the solvent, and trace amounts of acetaldehyde and vinyl acetate as by-products are evaporated when introduced from the high-temperature and high-pressure reactor to the low-pressure evaporator and sent to the refining step. Meanwhile, a liquid containing the rhodium compound as the other one of the principal catalysts is withdrawn from the bottom of the evaporator and circulated to the reactor to be used again. In this step, the evaporator may be either a flash evaporation type or a distillation column type with one or more plates (at least one plate). In order to lower the acetaldehyde and/or vinyl acetate content of the liquid circulated from the bottom of the evaporator to the reactor, however, the evaporator is preferably of the distillation column type. When the evaporator is of the distillation column type, the acetaldehyde and/or vinyl acetate content of the liquid to be circulated from the bottom of the evaporator to the reactor can be lowered to a greater extent to decrease the amount of tar formed. In other words, the impurities may advantageously be separated and removed through distillation in the evaporator of the distillation column type instead of flash evaporation.

The liquid fraction not evaporated in the evaporator and containing rhodium, promoter, etc., is returned to the reactor. A trace amount of ethylidene diacetate causative of tar formation is concentrated in this liquid, but ethylidene diacetate easily decomposes in water. Ethylidene diacetate is converted into vinyl acetate as a trace component having a very low boiling point through decomposition thereof with water, but vinyl acetate is easily distilled and separated in the evaporation vessel. Accordingly, a suitable amount of water may be added to the liquid fraction not evaporated in the evaporator. However, addition of water to the liquid not evaporated in the evaporator changes the acetic acid to acetic anhydride production ratio. In this case, the balance between acetic acid and acetic anhydride in the production thereof is controlled with methanol and methyl acetate and/or dimethyl ether and/or water fed into the reactor. The method of adding water to the liquid not evaporated in the evaporator vessel may be either mere direct feeding of water into a bottoms withdrawal piping of the evaporator or provision of a hydrolysis reactor. temperature of hydrolysis is preferably 10° to 300° C.

In the refining step, methyl iodide, methyl acetate, dimethyl ether, etc., as comparatively low-boiling components evaporated from the evaporator are separated in the first distillation column (3) and returned to the reactor to be used again. Part of the acetaldehyde and/or vinyl acetate causative of tar formation is contained in the distillate from the distillation column and composed of the comparatively low-boiling components, when the distillate is circulated to the reactor. Accordingly, vinyl acetate is preferably withdrawn as much as possible as a bottom product from the First distillation column by adopting a sufficient number of plates and/or reflux ratio in the first distillation column.

The liquid mixture of comparatively high-boiling acetic acid and acetic anhydride is separated into respective products in the second distillation column (4). Where vinyl acetate is withdrawn as a bottom product from the first distillation column, it must be separated and removed from the product acetic acid and product acetic anhydride in the second distillation column. Specific methods of separating vinyl acetate from product acetic acid and product acetic anhydride in the second distillation column include a method wherein low-boiling components causative of tar formation are distilled from the top of the second distillation column and acetic acid is separated as a sidestream withdrawn from a position below the feed plate of the second distillation column, while acetic anhydride is withdrawn as a bottom product from the bottom of the second distillation column; and a method wherein the mixture of acetic acid and acetic anhydride is withdrawn from the second distillation column and then separated and refined into product acetic acid and product acetic anhydride in another distillation column.

On the other hand, a trace amount of acetaldehyde contained in the liquid distilled from the first distillation column, and comprising methyl iodide, methyl acetate and dimethyl ether, is distilled and removed in the third distillation column (5), while methyl iodide, methyl acetate and dimethyl ether are withdrawn as bottom products from the third distillation column and circulated to the reactor to be used again. In the foregoing distillation procedure, separation and removal of acetaldehyde and separation and removal of vinyl acetate may be adopted either alone or in combination with each other. According to a conventional procedure, a liquid is directly circulated from the first distillation column to a reactor to contain large amounts of vinyl acetate and acetaldehyde. By contrast, distillation and separation of acetaldehyde in the third distillation column enable the amount of tar formed to be decreased.

The method of removing trace impurities causative of tar formation through distillation in the evaporator of distillation column type, the method of withdrawing vinyl acetate as a bottom product as much as possible from the first distillation column 3, and the method of distilling and removing acetaldehyde the third distillation column B may be employed either alone or in combination with each other. However, they are preferably employed in combination with each other.

EXAMPLE

The following Examples will specifically illustrate the present invention, but should not be construed as limiting the scope of the invention.

Example 1

A continuous withdrawal type autoclave was charged with 420 g/hr of a catalyst solution (0.94 wt. % $RhI_3$, 7.8 wt. % LiI, 45.6 wt. % acetic acid, and 45.6 wt. % acetic anhydride), 140 g/hr of methyl acetate, 140 g/hr of methyl iodide and 21 g/hr of methanol, and pressurized to a CO pressure of 17 atm and a hydrogen pressure of 2 atm and heated up to a temperature of 185° C. A liquid was continuously withdrawn from the autoclave and fed into an evaporator kept under a pressure of 2.4 atm at a temperature of 130° C. In the evaporator, acetic anhydride as the product, methyl iodide as the catalyst, unreacted methyl acetate and dimethyl ether, acetic acid as the solvent, and a trace amount of by-products were evaporated by flash evaporation and fed to the refining step. The liquid fraction not evaporated in the evaporator were recycled to the reactor since they contained rhodium, the promoter, etc. The fraction evaporated from the evaporator was fed to the first distillation column with 40 effective plates to effect separation thereof at a reflux ratio of 3. The distillate from the first distillation column was recycled as such to the reactor, while the bottoms from the first distillation column were fed to the second distillation column. In this Example, the proportion of tar formed as a by-product was 0.002 g (tar)/100 g (product acetic acid+product acetic anhydride).

Example 2

Substantially the same procedure as that of Example 1 was repeated except that the fraction evaporated from the evaporator was fed to the first distillation column with 60 effective plates to effect separation thereof at a reflux ratio of 3. In this case, the separability of vinyl acetate in the first distillation column was improved to decrease the amount of vinyl acetate circulated in the reaction system to 16% of that in Example 1. The proportion of tar formed as a by-product was 0.0004 g (tar)/100 g (product acetic acid + product acetic anhydride).

Example 3

Substantially the same procedure as that of Example 1 was repeated except that the reflux ratio in the first distillation column was altered to 5. In this case, the separability of vinyl acetate in the first distillation column was improved to decrease the amount of vinyl acetate circulated in the reaction system to 42% of that of Example 1. The proportion of tar formed as a by-product was 0.001 g (tar)/100 g (product acetic acid + product acetic anhydride).

Example 4

Substantially the same procedure as that of Example 1 was repeated except that the extent of firing in the first distillation column was a little controlled to make the amount of methyl acetate withdrawn as a bottom product from the bottom of the first distillation column 10 times as much as that of Example 1 and the distillate from the first distillation column was fed to the third distillation column, from the top of which acetaldehyde was distilled off. Acetic acid and acetic anhydride were withdrawn as bottom products from the first distillation column and separated from each other in the second distillation column to make respective products. In this case, the amount of vinyl acetate circulated in the reaction system was decreased to 4.8% of that of Example 1. The proportion of tar formed as a by-product was 0.0001 g (tar)/100 g (product acetic acid + product acetic anhydride).

Example 5

Substantially the same procedure as that of Example 1 was repeated except that a distillation column with 15 effective plates was used as the evaporator at a reflux ratio of 1. In this case, the amount of vinyl acetate circulated in the reaction system was decreased to 10% of that of Example 1. The proportion of tar formed as a by-product was 0.0002 g (tar)/100 g (product acetic acid + product acetic anhydride).

Example 6

Substantially the same procedure as that of Example 1 was repeated except that water was added in a molar amount of 10 times as much as that of the ethylidene diacetate contained in the bottoms from the evaporator to the bottoms from the evaporator midway of a piping and that no methanol was fed to the reactor. The proportion of tar formed as a by-product was 0.001 g (tar)/100 g (product acetic acid+ product acetic anhydride).

What is claimed is:

1. A process for producing acetic anhydride comprising the steps of:

continuously reacting at least one of dimethyl ether and methyl acetate with carbon monoxide in the presence of a rhodium compound and methyl iodide in a carbonylation reactor to form a resulting liquid reaction mixture; introducing the resulting liquid reaction mixture into an evaporator having a pressure lower than that of the reactor to separate the liquid reaction mixture into a volatile phase containing acetic anhydride, methyl iodide and at least one of unreacted dimethyl ether and unreacted methyl acetate and a nonvolatile phase containing the rhodium compound; recirculating the nonvolatile phase containing the rhodium compound back into the reactor; distilling the volatile phase to obtain a product mixture containing acetic anhydride and a distillate containing methyl iodide and at least one of the unreacted dimethyl ether and unreacted methyl acetate; distilling the distillate to remove acetaldehyde therefrom and form a bottom liquid; recirculating the bottom liquid back into the reactor; and recovering said product mixture containing acetic anhydride.

2. The process of claim 1, wherein acetic acid is also produced by said process and at least one of water and methanol are present in the reactor during the reacting step.

3. The process of claim 1, wherein said product mixture additionally contains vinyl acetate and is introduced into a distillation column to separate the vinyl acetate from the acetic anhydride.

4. The process of claim 1, wherein the evaporator is a distillation column.

5. The process of claim 1, wherein hydrogen is present in the reactor during the reacting step.

6. The process of claim 2, wherein said product mixture additionally contains vinyl acetate and is introduced into a distillation column to separate the vinyl acetate from the acetic anhydride and acetic acid.

7. The process of claim 2, wherein the evaporator is a distillation column.

8. The process of claim 2, wherein the nonvolatile phase containing the rhodium compound is mixed with water prior to being introduced into the reactor.

9. The process of claim 2, wherein hydrogen is in the reactor during the reacting step.

10. A process for producing acetic anhydride comprising the steps of:

continuously reacting at least one of dimethyl ether and methyl acetate with carbon monoxide in the presence of a rhodium compound and methyl iodide in a carbonylation reactor to form a resulting liquid reaction mixture; introducing the resulting liquid reaction mixture into an evaporator having a pressure lower than that of the reactor to separate the liquid reaction mixture into a volatile phase containing acetic anhydride, methyl iodide and at least one of unreacted dimethyl ether and unreacted methyl acetate and a nonvolatile phase containing the rhodium compound and ethylidene diacetate; adding water to the nonvolatile phase to convert the ethylidene diacetate contained therein to vinyl acetate; recirculating the nonvolatile phase containing the rhodium compound and the vinyl acetate back into the reactor; distilling the volatile phase to obtain a product mixture containing acetic anhydride and a distillate containing methyl iodide and at least one of the unreacted dimethyl ether and unreacted methyl acetate; distilling the distillate to remove acetaldehyde therefrom and form a bottom liquid; recirculating the bottom liquid back into the reactor; and recovering said product mixture containing acetic anhydride.

11. The process of claim 10, wherein water is added to the nonvolatile phase in a hydrolysis reactor.

12. The process of claim 11, wherein hydrolysis is conducted in said hydrolysis reactor at a temperature of from 10 to 300° C.

13. The process of claim 10, wherein acetic acid is also produced by said process and at least one of water and methanol are present in the reactor during the reacting step.

14. The process of claim 10, wherein said process consists essentially of the recited steps.

* * * * *